United States Patent
Fujimoto et al.

(10) Patent No.: US 9,621,814 B2
(45) Date of Patent: Apr. 11, 2017

(54) IMAGE PICKUP FOR ENDOSCOPE AND METHOD FOR OPERATING IMAGE PICKUP SYSTEM FOR ENDOSCOPE

(71) Applicant: OLYMPUS CORPORATION, Tokyo (JP)

(72) Inventors: Takehide Fujimoto, Tokyo (JP); Kiyotaka Kanno, Saitama (JP); Yutaka Fujisawa, Akishima (JP); Kotaro Ogasawara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/069,320

(22) Filed: Mar. 14, 2016

(65) Prior Publication Data

US 2016/0198076 A1 Jul. 7, 2016

Related U.S. Application Data

(63) Continuation of application No. PCT/JP2014/078188, filed on Oct. 23, 2014.

(30) Foreign Application Priority Data

Oct. 31, 2013 (JP) .................. 2013 227253

(51) Int. Cl.
*H04N 5/235* (2006.01)
*G02B 7/28* (2006.01)
(Continued)

(52) U.S. Cl.
CPC ............ *H04N 5/2352* (2013.01); *G02B 7/09* (2013.01); *G02B 7/28* (2013.01); *G02B 7/36* (2013.01);
(Continued)

(58) Field of Classification Search
CPC . H04N 5/2352; H04N 9/7908; H04N 5/23212
See application file for complete search history.

(56) References Cited

U.S. PATENT DOCUMENTS

| | | | | |
|---|---|---|---|---|
| 2012/0147165 | A1* | 6/2012 | Yoshino | H04N 5/23212 348/65 |
| 2013/0194485 | A1* | 8/2013 | Maruyama | H04N 9/7908 348/345 |
| 2014/0293038 | A1* | 10/2014 | Delmonico | H04N 5/2256 348/82 |

FOREIGN PATENT DOCUMENTS

| | | |
|---|---|---|
| JP | 2006-23652 A | 1/2006 |
| JP | 2006-324985 A | 11/2006 |

(Continued)

OTHER PUBLICATIONS

Japanese Office Action dated Aug. 4, 2015 received in Japanese Patent Application No. 2015-525660 with English-language translation.

(Continued)

*Primary Examiner* — Tung Vo
*Assistant Examiner* — Rowina Cattungal
(74) *Attorney, Agent, or Firm* — Scully, Scott, Murphy & Presser, PC (57) ABSTRACT

There is provided an image pickup system for endoscope including: a light source; an image forming optical system; a focus lens driving section; an image pickup section outputting an image signal; an image signal amplifying section; an image brightness detecting section; a brightness adjusting section adjusting a brightness control condition such as a light quantity of the light source, an image pickup condition of the image pickup section and an amplification factor of the amplifying section so that brightness of an image becomes a predetermined brightness; an auxiliary AF section estimating a temporary focus position based on the (Continued)

brightness control condition; a control section setting a small scanning range including the temporary focus position; and a contrast AF section causing contrast AF to be performed in the scanning range.

5 Claims, 9 Drawing Sheets

(51) Int. Cl.
| | | |
|---|---|---|
| *G02B 7/36* | (2006.01) | |
| *H04N 5/232* | (2006.01) | |
| *G02B 7/09* | (2006.01) | |
| *G03B 13/36* | (2006.01) | |
| *H04N 5/225* | (2006.01) | |
| *G03B 15/03* | (2006.01) | |

(52) U.S. Cl.
CPC ......... *H04N 5/2256* (2013.01); *H04N 5/2351* (2013.01); *H04N 5/23212* (2013.01); *G03B 13/36* (2013.01); *G03B 15/03* (2013.01); *H04N 2005/2255* (2013.01)

(56) References Cited

FOREIGN PATENT DOCUMENTS

| | | |
|---|---|---|
| JP | 2008-111897 A | 5/2008 |
| JP | 2009-133903 A | 6/2009 |
| JP | 2009-186894 A | 8/2009 |
| JP | 2012-108313 A | 6/2012 |

OTHER PUBLICATIONS

International Search Report dated Jan. 27, 2015 received in International Application No. PCT/JP2014/078188.

* cited by examiner

IMAGE PICKUP FOR ENDOSCOPE AND METHOD FOR OPERATING IMAGE PICKUP SYSTEM FOR ENDOSCOPE

CROSS REFERENCE TO RELATED APPLICATION

This application is a continuation application of PCT/JP2014/078188 filed on Oct. 23, 2014 and claims benefit of Japanese Application No. 2013-227253 filed in Japan on Oct. 31, 2013, the entire contents of which are incorporated herein by this reference.

BACKGROUND OF THE INVENTION

1. Field of the Invention

The present invention relates to an image pickup system for endoscope which radiates illuminating light to a subject existing at a dark place to perform contrast AF, and a method for operating the image pickup system for endoscope.

2. Description of the Related Art

As ranging methods for acquiring information about a distance to a subject, an active method in which infrared, ultrasound or the like is radiated to the subject, and a distance is detected based on a time period required for a reflected wave to return or a radiation angle, and a passive method in which ranging is performed with use of an image acquired via an optical system without using infrared or the like are known.

Examples of the passive method of the methods include phase-difference AF (AF: autofocus) used in single-lens reflex cameras and the like and contrast AF widely used in video cameras, compact-type cameras and the like.

The phase-difference AF is not so often used in small-sized image pickup apparatuses because, though focusing speed is relatively high, the phase-difference AF utilizes a luminous flux which has passed through an objective lens and, therefore, for example, such a configuration is adopted that the luminous flux is caused to branch to a phase-difference AF sensor side, the phase-difference AF sensor being different from an image pickup section which picks up an image.

On the other hand, the contrast AF does not require a separate AF sensor or the like because the contrast AF utilizes an image picked up by the image pickup section to perform AF. Therefore, the contrast AF is adopted in small-sized image pickup apparatuses. In order to determine a focus position (a peak position of an AF evaluation value (contrast or the like)) in the contrast AF, it becomes necessary to perform scanning for acquiring a plurality of (generally, three or more) frame images while causing a position of a focus lens to change. Especially, in a case of scanning a whole scanning range, a whole range within which the focus lens can be driven, the number of acquired images increases, and a long photographing time period is required.

Thus, it has been proposed to reduce the number of frame images required before being focused in the contrast AF.

For example, Japanese Patent Application Laid-Open Publication No. 2008-111897 describes an example of an operation in a mode in which a wire net or a cage existing in a vicinity is prevented from being focused, and describes a technique in which a distance to the wire net or the like is measured based on an output of a line sensor which performs phase-difference AF, a vicinity of the measured distance to the wire net or the like is excluded as a ranging range, and contrast AF is performed in a ranging range other than the ranging range while a position of a focus lens is being changed.

Further, Japanese Patent Application Laid-Open Publication No. 2009-133903 describes a technique in which an predicted focus position is calculated based on a size of a target object detected by a target object detecting section (such as a face detecting section), and contrast AF is performed with a vicinity of the calculated predicted focus position as a start point of movement of a focus lens.

Both of the techniques described in the respective patent gazettes aim to shorten a focusing time period by, when performing contrast AF, acquiring a distance to an object by performing auxiliary measurement to eliminate necessity of causing the focus lens to move in the whole scanning range.

SUMMARY OF THE INVENTION

An image pickup system for endoscope according to a certain aspect of the present invention includes: a light source radiating illuminating light to a subject; an image forming optical system forming an optical image of reflected light reflected from the subject out of the illuminating light radiated by the light source; a driving section driving a focus lens, the focus lens being a part of the image forming optical system, within a predetermined movable range; an image pickup section picking up the optical image formed by the image forming optical system and outputting an image signal; an amplifying section signal-amplifying the image signal outputted from the image pickup section according to an amplification factor; a brightness detecting section detecting brightness of the image indicated by the image signal; a brightness adjusting section adjusting a brightness control condition for, if the brightness of the image detected by the brightness detecting section changes, controlling at least one parameter among a condition of a light quantity by the light source, a condition of image pickup by the image pickup section and the amplification factor of the amplifying section so that the brightness of the image becomes a predetermined brightness; an auxiliary autofocus section estimating a temporary focus position of the optical image based on the brightness control condition adjusted by the brightness adjusting section; a control section setting a range which includes the temporary focus position and which is smaller than the predetermined movable range as a scanning range of contrast autofocus; and a contrast autofocus section causing the driving section to drive the focus lens to perform contrast autofocus within the scanning range.

A method for operating an image pickup system for endoscope according to a certain aspect of the present invention includes the steps of: radiating illuminating light to a subject, by a light source; driving a focus lens, the focus lens being a part of an image forming optical system forming an optical image of reflected light reflected from the subject out of the illuminating light radiated by the light source, within a predetermined movable range, by a driving section; picking up the optical image formed by the image forming optical system and outputting an image signal, by an image pickup section; signal-amplifying the image signal outputted from the image pickup section according to an amplification factor, by an amplifying section; detecting brightness of the image indicated by the image signal, by a brightness detecting section; adjusting a brightness control condition for, if the brightness of the image detected by the brightness detecting section changes, controlling at least one parameter among a condition of a light quantity by the light source, a condition of image pickup by the image pickup section and the amplification factor of the amplifying section so that the brightness of the image becomes a predetermined brightness, by a brightness adjusting section; estimating a temporary focus position of the optical image based on the brightness control condition adjusted by the brightness adjusting section, by an auxiliary autofocus section; setting a range which includes the temporary focus position and which is smaller than the predetermined movable range as a scanning range of contrast autofocus, by a control section; and causing the driving section to drive the focus lens to perform contrast autofocus within the scanning range, by a contrast autofocus section.

DETAILED DESCRIPTION OF THE PREFERRED EMBODIMENTS

Embodiments of the present invention will be described below with reference to drawings.

First Embodiment

Figure 1:
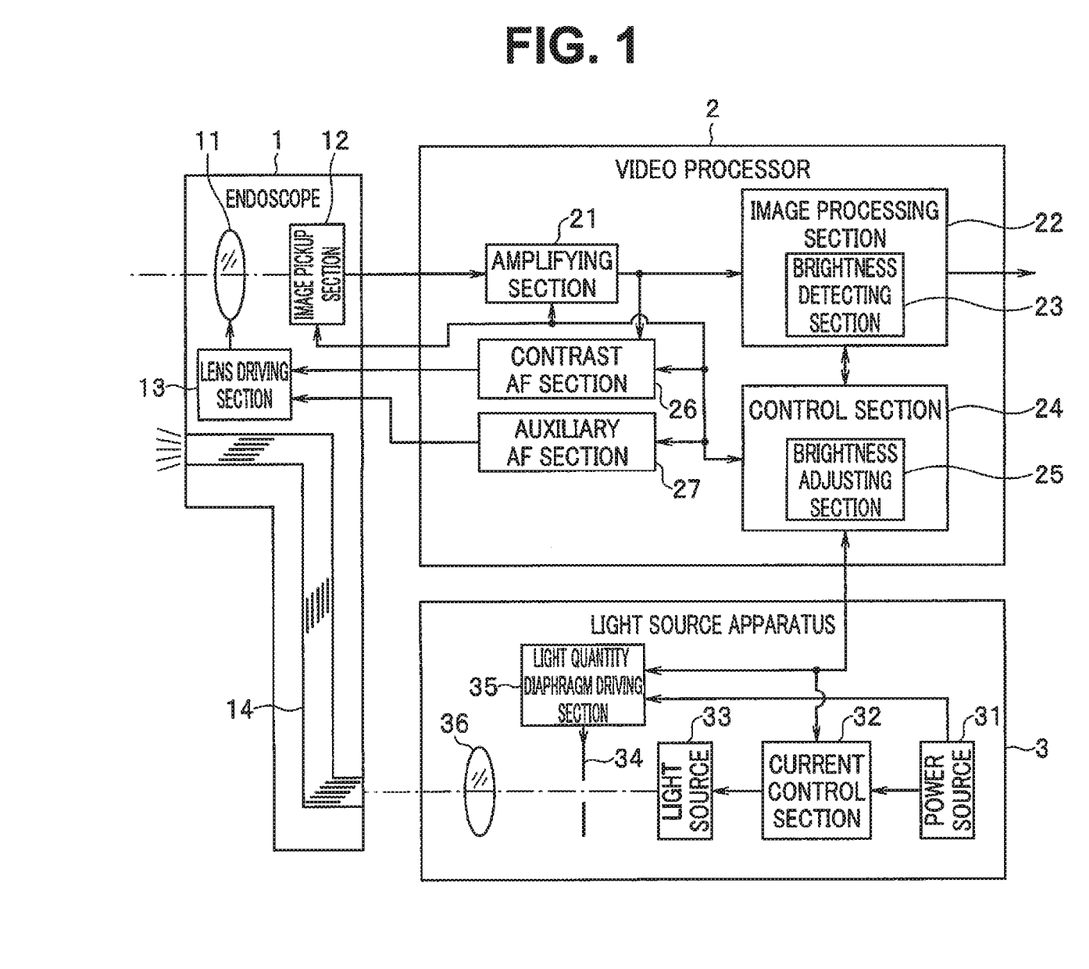
FIG. 1 is a block diagram showing a configuration of an image pickup system in a first embodiment of the present invention.
Figure 2:
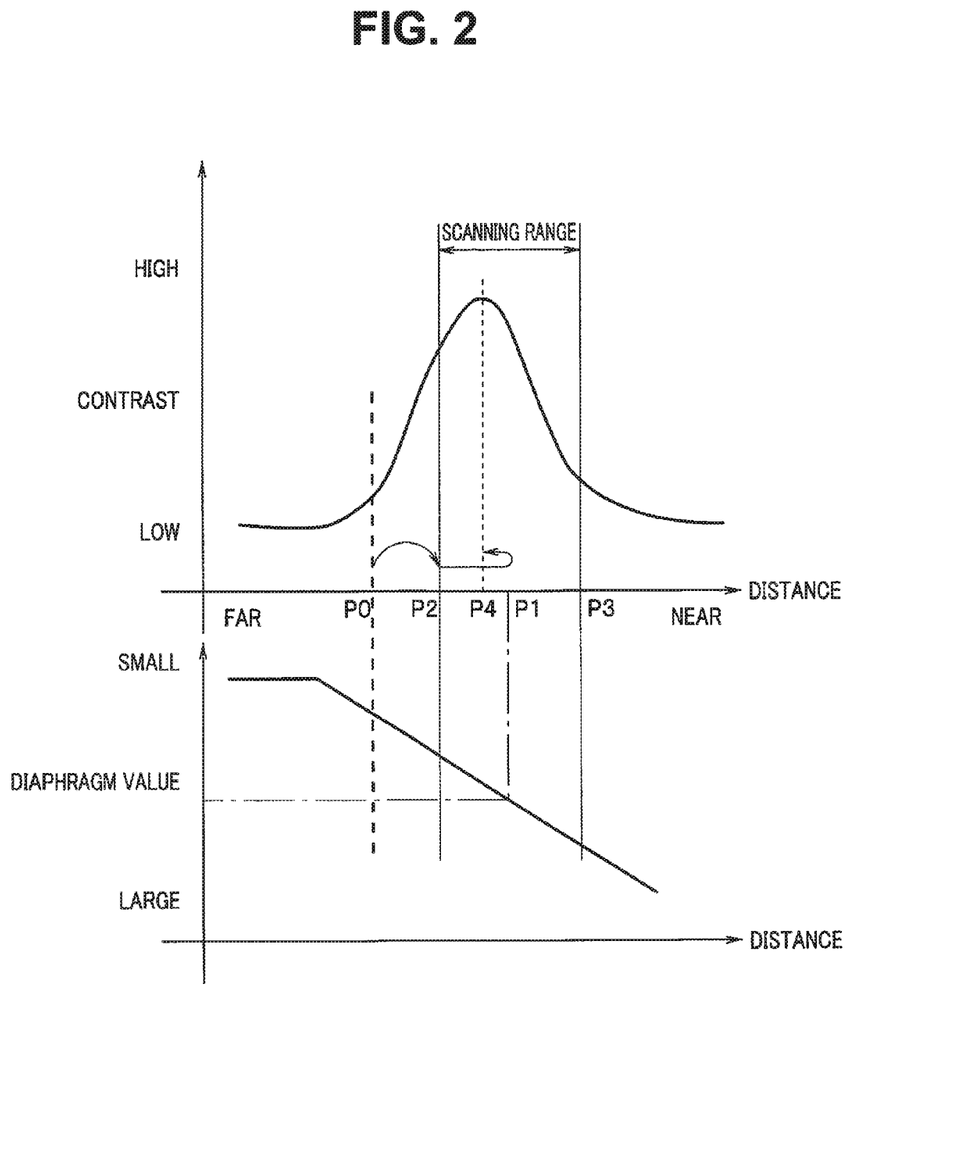
FIG. 2 is a chart showing an example of setting a scanning range in contrast AF based on a brightness control condition at a time when brightness of an image becomes a predetermined brightness in the first embodiment.
Figure 3:
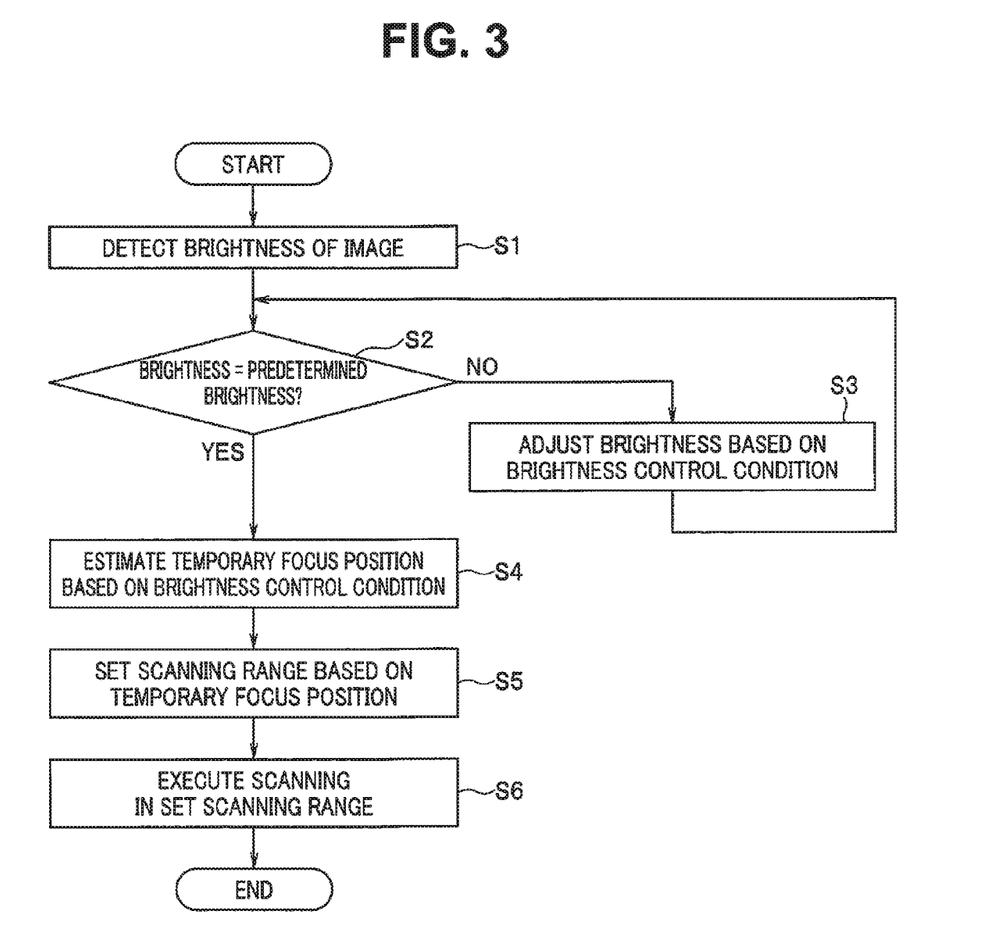
FIG. 3 is a flowchart showing an operation of the image pickup system in the first embodiment.

FIGS. 1 to 3 show a first embodiment of the present invention, and FIG. 1 is a block diagram showing a configuration of an image pickup system.

The image pickup system is for observing a subject existing at a dark place. The image pickup system is provided with an endoscope 1, a video processor 2 and a light source apparatus 3, and is configured, for example, as an endoscope system.

The endoscope 1 is provided with an image forming optical system 11, an image pickup section 12, a lens driving section 13 and a light guide 14.

The image forming optical system 11 forms an optical image of a subject and is an optical system which is provided with a focus lens and the like and in which a focus position is variable. Note that the image forming optical system 11 may be an optical system which is further provided with a zoom lens and the like and in which a zoom position is variable.

The image pickup section 12 picks up an optical image formed by the image forming optical system 11 and outputs the image. At this time, an exposure time period at the time of the image pickup section 12 picking up the image is variable, for example, based on control of a control section 24 to be described later.

The lens driving section 13 drives the image forming optical system 11 in order to cause the focus position and the like to change. More specifically, the lens driving section 13 causes the focus position to change by driving the focus lens, and, if the zoom lens is provided, causes the zoom position to change by driving the zoom lens.

The light guide 14 transmits illuminating light supplied from the light source apparatus 3 to a distal end of an insertion portion of the endoscope 1. The illuminating light transmitted in this way is radiated to a subject existing at a dark place from the distal end of the insertion portion of the endoscope 1.

The video processor 2 control-drives the endoscope 1 and processes an image obtained from the endoscope 1. The video processor 2 is provided with an amplifying section 21, an image processing section 22, the control section 24, a contrast AF section 26 and an auxiliary AF section 27.

The amplifying section 21 performs signal amplification of an image outputted from the image pickup section 12 according to a set amplification factor.

The image processing section 22 performs various kinds of image processing, such as color signal processing, color space conversion processing, edge enhancement processing, noise reduction processing, overexposure state prevention processing, white balance processing and γ conversion, for the image signal-amplified by the amplifying section 21. The image processed by the image processing section 22 is outputted to a monitor or a recording device. The image processing section 22 is further provided with a brightness detecting section 23 which detects brightness of an image.

The control section 24 controls each section in the video processor 2 as well as controlling the endoscope 1 and the light source apparatus 3. The control section 24 is configured including, for example, a CPU and the like. That is, the control section 24 sets an amplification factor to cause the amplifying section 21 to signal-amplify an image, controls the image processing section 22 to perform the various kinds of image processing described above, controls the auxiliary AF section 27 to perform auxiliary AF, sets a range which includes a temporary focus position obtained as a result of the auxiliary AF and which is smaller than a whole scanning range as a scanning range of contrast AF, and causes the contrast AF section 26 to perform contrast AF within the set scanning range.

The control section 24 is provided with a brightness adjusting section 25 which adjusts brightness of an image based on a brightness control condition. The brightness adjusting section 25 automatically performs adjustment so that brightness of an image detected by the brightness detecting section 23 becomes, for example, a predetermined brightness. Here, the brightness control condition is a light quantity condition for illuminating light the light source apparatus 3 supplies, the exposure time period of the image pickup section 12, the amplification factor in the amplifying section 21 or the like.

The contrast AF section 26 causes the image pickup section 12 to acquire a plurality of (generally three or more) images while causing the focus position to change within the scanning range set by the control section 24, calculates a contrast evaluation value of each of the acquired images, and adjusts the focus position so that the contrast evaluation value takes a peak value.

The auxiliary AF section 27 estimates a temporary focus position of an optical image of a subject based on brightness of an image (further based on the brightness control condition as necessary). More specifically, in the case where the brightness adjusting section 25 automatically adjusts brightness of an image to the predetermined brightness, the auxiliary AF section 27 estimates the temporary focus position of the optical image of the subject based on a brightness control condition a time when the brightness of the image is the predetermined brightness.

The light source apparatus 3 supplies illuminating light to be radiated to a subject existing at a dark place, for example, with a variable light quantity, and is provided with a power source 31, a current control section 32, a light source 33, a light quantity diaphragm 34, a light quantity diaphragm driving section 35 and a collimator lens 36.

The power source 31 supplies a current to each section in the light source apparatus 3. The power source 31 supplies a current, for example, to the current control section 32 and the light quantity diaphragm driving section 35.

The current control section 32 controls a current to be supplied to the light source 33 based on control of the control section 24 described above.

The light source 33 emits light by receiving supply of the current from the current control section 32 and is configured including, for example, a lamp such as a halogen lamp, a xenon lamp and a metal halide lamp, or a semiconductor light emitting device such as an LED. Note that, if the light source 33 is configured including a semiconductor light emitting device such as an LED, the current control section 32 described above is configured so as to be able to control the light quantity of illuminating light by pulse-width control (so-called PWM). A pulse width in the pulse-width control of the current control section 32 is one of the light quantity conditions described above.

The light quantity diaphragm 34 is for controlling the light quantity of illuminating light. A diaphragm value of the light quantity diaphragm 34 is one of the light quantity conditions described above.

The light quantity diaphragm driving section 35 drive-controls the light quantity diaphragm 34 based on control of the control section 24 so that a diaphragm value specified by the light quantity condition is obtained.

The collimator lens 36 converts illuminating light which has been emitted from the light source 33 and the light quantity of which has become a predetermined light quantity via the light quantity diaphragm 34, to a parallel luminous flux and radiates the parallel luminous flux to an incident end of the light guide 14.

Next, FIG. 2 is a chart showing an example of setting the scanning range in contrast AF based on the brightness control condition at the time when brightness of an image becomes the predetermined brightness, and FIG. 3 is a flowchart showing an operation of the image pickup system.

When a process shown in FIG. 3 is started, the brightness detecting section 23 detects brightness of an image (step S1).

Then, the control section 24 determines whether the detected brightness is a predetermined brightness or not (step S2).

Here, if it is determined that the detected brightness is not the predetermined brightness, the brightness adjusting section 25 adjusts the brightness of the image based on a brightness control condition (step S3). More specifically, if the image is darker than the predetermined brightness, the brightness adjusting section 25 performs adjustment so that the brightness of the image becomes the predetermined brightness by performing at least one of increasing an opening (decreasing a diaphragm value) of the light quantity diaphragm 34, increasing the pulse width of pulse-width control, lengthening the exposure time period of the image pickup section 12, increasing the amplification factor of the amplifying section 21 and the like. Further, if the image is brighter than the predetermined brightness, the brightness adjusting section 25 performs opposite adjustment to the above-described adjustment.

If it is determined at step S2 that the brightness of the image is the predetermined brightness, the auxiliary AF section 27 estimates a temporary focus position of an optical image of a subject based on a brightness control condition at the time when the brightness becomes the predetermined brightness (step S4).

Here, description will be made on a case where the brightness control condition for adjusting the brightness of the image is the diaphragm value of the light quantity diaphragm 34, and the brightness adjusting section 25 adjusts the brightness of the image to the predetermined brightness by changing the diaphragm value as a specific example with reference to FIG. 2. In a case where the brightness control condition is the pulse width in the pulse-width control, the exposure time period of the image pickup section 12, the amplification factor of the amplifying section 21 or the like as described above, in addition to the diaphragm value, or the brightness control condition is a combination among them, a similar process can be also performed.

First, when the light quantity of illuminating light supplied from the light source apparatus 3 to the endoscope 1 is kept constant, the light quantity of illuminating light radiated to the subject changes according to a distance from a distal end face of the insertion portion of the endoscope 1 to the subject. For example, the light quantity is in inverse proportion to a subject distance squared. Accordingly, brightness of a subject existing at a dark place, which is an observation target of the image pickup system of the present embodiment, and, therefore, brightness of an image obtained by picking up an image of the subject changes according to a subject distance. That is, the subject distance is indicated by a function of the brightness of the image.

On the other hand, the image pickup system is, for example, provided with an automatic light adjustment system for picking up an image of a subject with continuously constant brightness. In the image pickup system of the present embodiment, it is the brightness adjusting section 25 and the like that are responsible for the function of the automatic light adjustment system.

In the case where the brightness control condition is the diaphragm value of the light quantity diaphragm 34, the opening of the light quantity diaphragm 34 is large when the diaphragm value is small, and, therefore, the light quantity of illuminating light supplied from the light source apparatus 3 increases. On the contrary, when the diaphragm value is large, the opening of the light quantity diaphragm 34 is small, and, therefore, the light quantity of the illuminating light supplied from the light source apparatus 3 decreases.

Therefore, the brightness adjusting section 25 decreases the diaphragm value to increase the light quantity of illumination if a subject exists far away and brightness of an image is lower than the predetermined brightness, and increases the diaphragm value to decrease the light quantity of illumination if a subject exists nearby and brightness of an image is higher than the predetermined brightness.

The auxiliary AF section 27 acquires the diaphragm value at the time when the predetermined brightness is obtained in this way, from the control section 24. As described above, a subject distance is indicated by the function of brightness of an image, and the brightness of the image is indicated by a function of diaphragm value. That is, the subject distance is indicated by the function of diaphragm value (more generally, a subject distance is indicated by a multivariable function of a brightness control condition as described above).

It is assumed that the function between the diaphragm value and the subject distance is, for example, as shown in a diaphragm value-distance graph shown on a lower side of FIG. 2. The diaphragm value-distance graph shows that, as the subject distance is nearer, the diaphragm value is increased (an opening diameter of the light quantity diaphragm 34 is decreased) to decrease the light quantity of illumination.

When such a relationship between the diaphragm value and the subject distance exists, the auxiliary AF section 27 calculates a distance corresponding to the diaphragm value at the time when the brightness of the image becomes the predetermined brightness. Here, it is assumed that the calculated distance is P1. The auxiliary AF section 27 sets P1 calculated in this way as the temporary focus position.

Next, the auxiliary AF section 27 decides, for example, a range from P2 to P3 which is smaller than a whole scanning range as a scanning range in contrast AF such that the calculated temporary focus position P1 is included (step S5).

Though the scanning range from P2 to P3 may be decided so that a predetermined range is set on each of a near-distance side and a far-distance side with the temporary focus position P1 as a center, it is better to adaptively decide the scanning range from P2 to P3 in consideration of other conditions. For example, when an image blur is considered, the blur increases if the diaphragm opening diameter of the image forming optical system 11 is large. Therefore, it is also possible to increase the predetermined range when the diaphragm opening diameter of the image forming optical system 11 is large and decrease the predetermined range when the diaphragm opening diameter is small. Further, since the size of the blur increases more easily on the near-distance side than the far-distance side, it is also possible to set the predetermined range on the near-distance side of the temporary focus position larger than the predetermined range on the far-distance side of the temporary focus position.

Receiving information about the scanning range from P2 to P3 decided by the auxiliary AF section 27, the contrast AF section 26 causes the focus position to move from a current focus position P0 to an appropriate scanning start position in the scanning range from P2 to P3, here, P2 which is the nearest to the focus position P0 (however, it is also possible to perform movement to the scanning start position by the auxiliary AF section 27 and, after that, start scanning by the contrast AF section 26). Since the position P2 is a point at a farthest distance in the scanning range from P2 to P3, scanning is started toward the near-distance side. By reversing a scanning direction when the contrast evaluation value begins to decrease after gradually increasing, the focus position can be adjusted to a true focus position P4 where the contrast evaluation value takes a peak value (step S6).

As a result of performing scanning in this way, the process ends when the focus position P4 is reached.

Note that, since the subject distance is indicated by the function of brightness of an image as described above, the auxiliary AF section 27 can estimate a temporary focus position based on brightness of an image even in a case where the brightness adjusting section 25 does not automatically adjust the brightness of the image to a predetermined brightness. Therefore, the estimation of the temporary focus position by the auxiliary AF section 27 is not limited to use of a brightness control condition at the time when brightness of an image becomes a predetermined brightness.

Thus, in the case of a subject existing at a dark place, which is an observation target of the image pickup system of the present embodiment, a relationship between brightness of an image and a subject distance occurs, and, therefore, the auxiliary AF section 27 performs AF referred to as brightness AF utilizing the relationship.

According to the first embodiment as described above, a temporary focus position is detected by performing auxiliary AF (brightness AF) before performing contrast AF, and a scanning range and a scanning start position in contrast AF are decided based on the detected temporary focus position. Here, since the decided scanning range is smaller than the whole scanning range, a time period required for focusing in contrast AF can be shortened. Since a final focus position is determined by contrast AF, highly precise focus detection becomes possible.

Further, since brightness AF based on an image acquired from the image pickup section 12 is used as auxiliary AF before performing contrast AF, another component, for example, a phase-difference AF sensor in a case of using phase-difference AF as the auxiliary AF is unnecessary, and, therefore, there is an advantage of being suitable for fields such as an endoscope field from which downsizing and diameter reduction are required.

Thus, it becomes possible to shorten the time period required for focusing a subject (an arbitrary subject with any size and in any shape) existing at a dark place in contrast AF.

By the way, in a case where the image forming optical system 11 is an optical system which is provided with a focus lens and a zoom lens and in which the focus position and the zoom position are variable, such a configuration is conventionally adopted that a total of four switches, a switch for causing the focus position to move to a near side, a switch for causing the focus position to move to a far side, a switch for causing the zoom position to move to a tele side and a switch for causing the zoom position to move to a wide side, are provided, for example, on an operation portion of the endoscope 1. However, since the number of switches is large in the configuration, it is troublesome for a surgeon to operate the switches. Further, it is difficult to grasp, only from an image being observed, a focus state and zoom state of the current image during use of the image pickup system, and there is room for improvement of usability.

Thus, a configuration in which one switch is used as the four switches will be described with reference to FIGS. 4 to 9.

Figure 4:
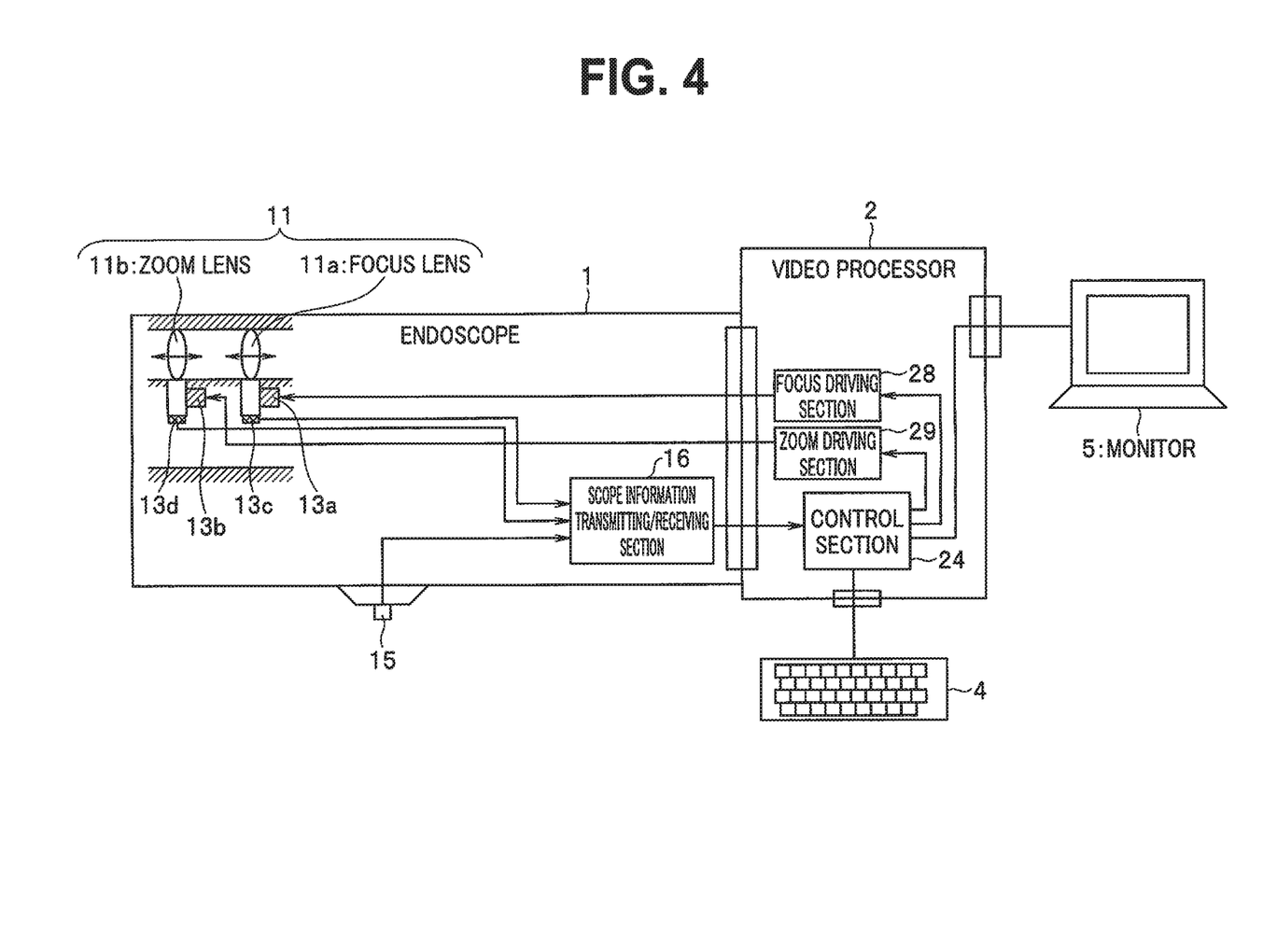
FIG. 4 is a diagram showing a configuration of an image pickup system provided with a focus/zoom switch in relation to the first embodiment.

FIG. 4 is a diagram showing a configuration of an image pickup system provided with a focus/zoom switch.

The image pickup system is provided with the endoscope 1 and the video processor 2 and further provided with an operation portion 4 and a monitor 5, and the image pickup system is configured, for example, as an endoscope system. Here, it is assumed that the light source apparatus 3 is further provided though it is not shown in FIG. 4.

The image forming optical system 11 of the endoscope 1 is provided with a focus lens 11a and a zoom lens 11b. The focus lens 11a and the zoom lens 11b are adapted to be driven by an actuator 13a and an actuator 13b, respectively. Further, a driven position and, therefore, the focus position of the focus lens 11a and a driven position and, therefore, the zoom position of the zoom lens 11b are detected by a position detecting section 13c and a position detecting section 13d, respectively. Here, as for detection of lens positions by the position detecting sections 13c, 13d, various kinds of methods, such as a method using a position sensor, a method of detecting an actuator resistance value and a method based on a count value of the number of drive pulses, can be appropriately adopted.

For example, the operation portion of the endoscope 1 is provided with a switch 15 which is a focus/zoom switch for both of a focus operation and a zoom operation. The switch 15 is configured, for example, as a push-operation-type push button switch.

Information about the focus position detected by the position detecting section 13c, information about the zoom position detected by the position detecting section 13d and information about a switch operation from the switch 15 are transmitted to the control section 24 of the video processor 2 via a scope information transmitting/receiving section 16 provided, for example, in the operation portion of the endoscope 1.

On the other hand, the video processor 2 is provided with a focus driving section 28 and a zoom driving section 29 in addition to the control section 24.

Based on control of the control section 24 which has obtained the information about the focus position and the switch operation, the focus driving section 28 drives the actuator 13a to cause the focus lens 11a to move in an optical axis direction and performs focus position adjustment.

Based on control of the control section 24 which has obtained the information about the zoom position and the switch operation, the zoom driving section 29 drives the actuator 13b to cause the zoom lens 11b to move in the optical axis direction and performs zoom position adjustment.

Further, the operation portion 4 is connected to the control section 24 and is configured so as to be able to set priority modes related to the switch 15 and input other various kinds of operations. Here, as the priority modes related to the switch 15, there are a focus priority mode and a zoom priority mode in which a focus function and a zoom function are prioritized, respectively, as an initial function of the switch 15 immediately after power is turned on, after the switching function is reset, and the like. Further, as for the focus function of the present configuration example, a selection can be made between a seamless operation in which the focus position can be caused to continuously change and a so-called two-focus switching in which the focus position is switched only between near and normal (a certain focus position on a far side of the "near"), and the selection of the focus function is also performed by the operation portion 4.

The control section 24 is further connected to the monitor 5. The monitor 5 displays an image acquired from the endoscope 1 and, by the control of the control section 24, further displays each of pieces of information about the priority mode, the focus position and the zoom position.

Figure 5:
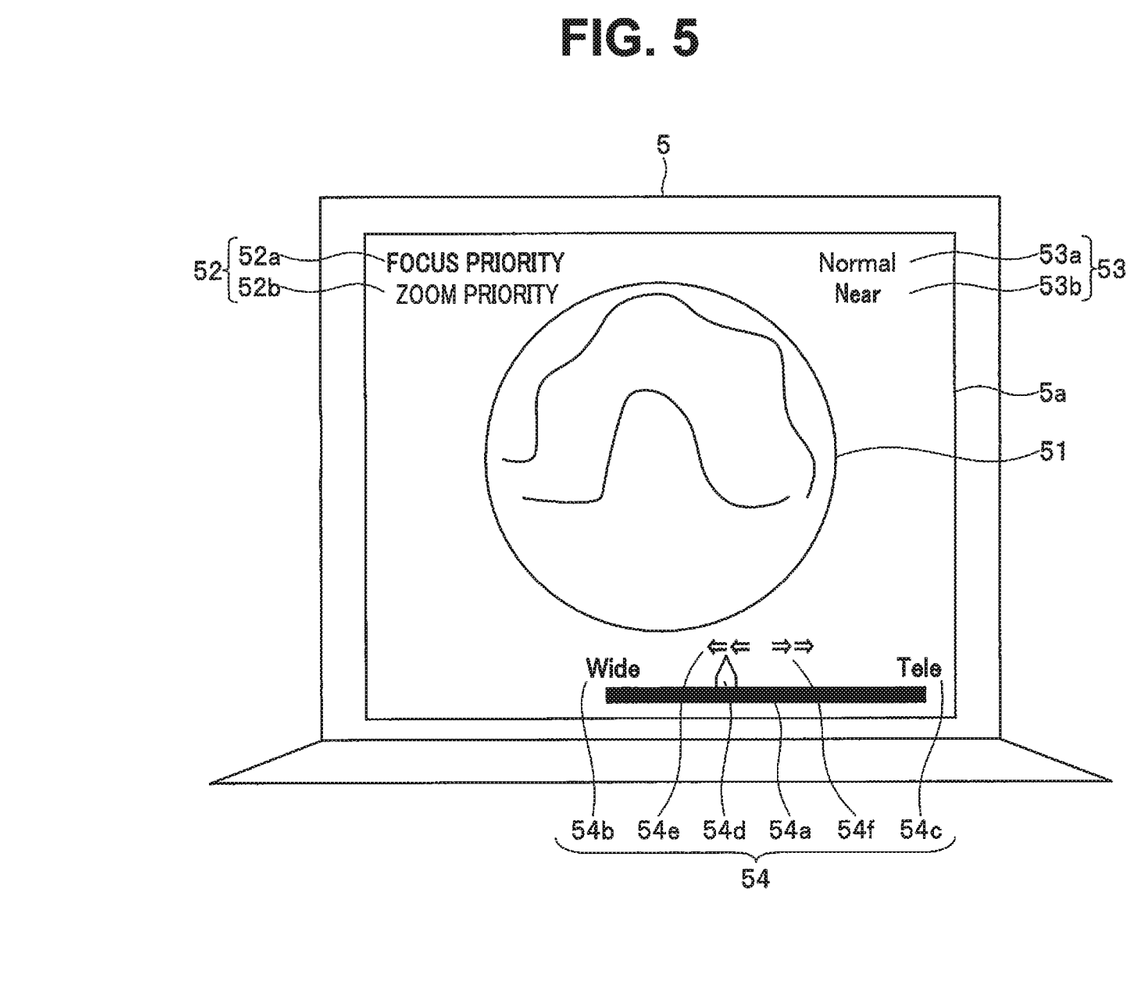
FIG. 5 is a diagram showing a display example of a monitor in relation to the first embodiment.

Here, FIG. 5 is a diagram showing a display example of the monitor 5.

On a screen 5a of the monitor 5, an endoscopic image 51 is displayed, for example, at a central part.

Further, for example, at an upper left part of the screen 5a, a priority mode display 52 including a focus priority mode display 52a and a zoom priority mode display 52b is displayed. In the example shown in FIG. 5, the focus priority mode display 52a is highlighted to indicate that the switch 15 is currently set to the focus priority mode.

Further, for example, at an upper right part of the screen 5a, a focus position display 53 including a normal focus position display 53a and a near focus position display 53b is displayed. In the example shown in FIG. 5, the near focus position display 53b is highlighted to indicate that the focus lens 11a currently exists at a near focus position.

In addition, for example, at a bottom side part of the screen 5a, a zoom position display 54 including a zoom position bar 54a, a wide position display 54b, a tele position display 54c, an indicator 54d, a wide direction display 54e and a tele direction display 54f is displayed. In the example shown in FIG. 5, the indicator 54d is displayed between the wide position display 54b and the tele position display 54c and a little closer to the "wide" to indicate a current zoom position, and the wide direction display 54e is highlighted to indicate that a movement direction in a case where the zoom lens 11b moves is currently set to a "wide" direction.

Note that, though it is assumed that the so-called two-focus switching in which only two points, normal and near, can be taken as the focus position is set in the display example shown in FIG. 5, display similar to the zoom position display 54 described above is also possible in the case of the seamless operation in which the focus position can be continuously changed. Further, an aspect of display is, of course, not limited to the example shown in FIG. 5.

Next, description will be made on how the focus state and zoom state of an image change according to an operation of the switch 15 with reference to FIGS. 6 to 9. Here, in FIGS. 6 to 9, each image state diagram is arranged on an assumption that, when a longitudinal direction of each drawing is seen as a right and left direction, a left side is a wide side, a right side is a tele side, an upper side is a normal side, and a lower side is a near side.

Further, in the present configuration example, there are a "short push" indicated by a solid line arrow, a "long push" indicated by a thick solid line arrow and "two successive short pushes" indicated by an arrow outline with a blank inside as operations of the switch 15 related to the focus state and the zoom state. Furthermore, settings related to the focus state and the zoom state are also performed by a "CPU process" (a process by the control section 24) indicated by a dotted-line arrow.

Note that, though description will be made on an assumption that, as for zooming, the seamless operation is performed in the present configuration example, this is not limiting, and a configuration in which a plurality of focal distances can be discontinuously taken, and the like are also possible.

Figure 6:
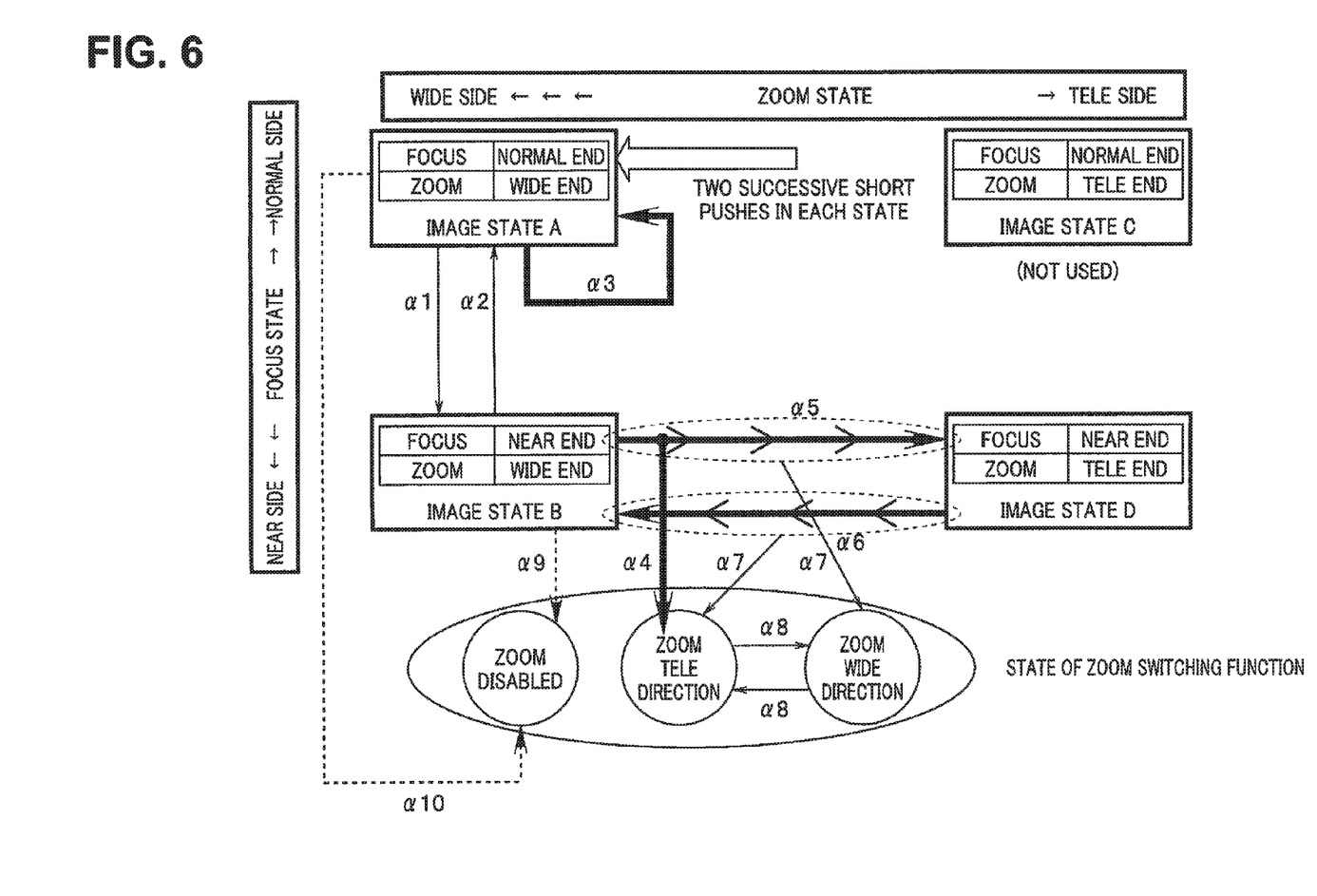
FIG. 6 is a diagram showing an operation of the image pickup system in a focus priority mode when two-focus switching is set for focusing, in relation to the first embodiment.

FIG. 6 is a diagram showing an operation of the image pickup system in the focus priority mode when the two-focus switching is set for focusing.

First, an image state A is a state in which focus is at a normal end, and zoom is at a wide end; an image state B is a state in which the focus is at a near end, and the zoom is at the wide end; an image state C is a state in which the focus is at the normal end, and the zoom is at a tele end; and an image state D is a state in which the focus is at the near end, and the zoom is at the tele end. The image state C among the states is not used in the focus priority mode when two-point switching is set for focusing as shown in FIG. 6.

When the image pickup system is powered on, the image state is switched to the image state A as an initial state. The image state A is suitable for panoramic observation.

When the switch 15 is pushed shortly in the image state A, the image state A is switched to the image state B as shown by an arrow α1.

Further, when the switch 15 is pushed shortly in the image state B, the image state B is switched to the image state A as shown by an arrow α2.

On the other hand, even if the switch 15 is pushed long in the image state A, the image state A does not change as shown by an arrow α3.

When the switch 15 is pushed long in the image state B, the function of the switch 15 is switched to a zoom tele direction function for changing the zoom state to the tele direction, as shown by an arrow α4.

If the function of the switch 15 is the zoom tele direction, the zoom state changes to the tele direction while the switch 15 is pushed long, as shown by an arrow α5. However, since the tele end is reached when the image state D is reached, the change of the zoom state to the tele direction does not advance any more.

If the function of the switch 15 is a zoom wide direction function for changing the zoom state to the wide direction in the image state D, or in a state between the image state B and the image state D, the zoom state changes to the wide direction while the switch 15 is pushed long as shown by an arrow α6.

If the function of the switch 15 is the zoom tele direction or the zoom wide direction, the zoom direction is switched when the switch 15 is pushed shortly, as shown by an arrow α7.

That is, the function of the switch 15 is switched to the zoom wide direction by pushing the switch 15 shortly when the function is the zoom tele direction, and switched to the zoom tele direction by pushing the switch 15 shortly when the function is the zoom wide direction, as shown by arrows α8.

If the image state B is reached as a result of the zoom state having changed to the wide direction by the operation shown by the arrow α6, the switch 15 is disabled to function as a zoom switch by a process in the CPU as shown by an arrow α9, that is, the switch 15 enters a state of functioning as a focus switch.

Further, no matter whether the image state is in any of the image state B, the state between the image state B and the image state D, and the image state D, the image state returns to the image state A when the operation of the "two successive short pushes" indicated by the arrow outline with a blank inside is performed by the switch 15. Therefore, panoramic observation similar to that at the time when power is turned on can be quickly performed by a simple operation. When the image state returns to the image state A, the switch 15 is disabled to function as a zoom switch by the process in the CPU and enters the state of functioning as a focus switch, as shown by an arrow α10.

Figure 7:
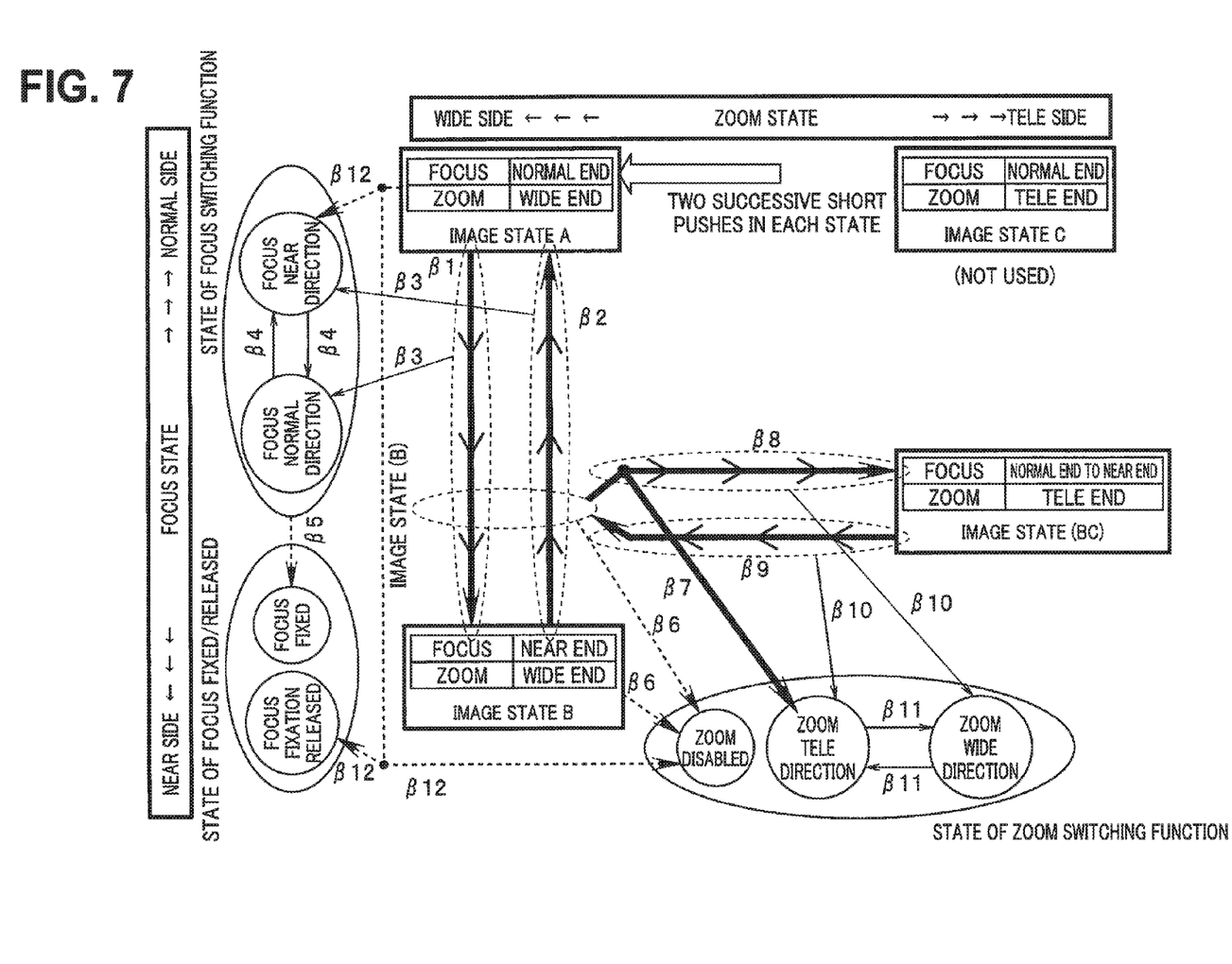
FIG. 7 is a diagram showing an operation of the image pickup system in the focus priority mode when a seamless operation is set for focusing, in relation to the first embodiment.

FIG. 7 is a diagram showing an operation of the image pickup system in the focus priority mode when the seamless operation is set for focusing.

First, image states A to C are similar to the above description; an image state (B) is a state in which focus is between the normal end and the near end, and zoom is at the wide end (a state between the image state A and the image state B); and an image state (BC) is a state in which the focus is between the normal end and the near end, and the zoom is at the tele end. Note that the image state C is also not used in the focus priority mode when the seamless operation is set for focusing as shown in FIG. 7.

When the image pickup system is powered on, the image state is switched to the image state A as an initial state.

When the switch 15 is pushed long when the function of the switch 15 is a focus near direction function for causing the focus state to change to the near direction in the image state A or in the state between the image state A and the image state B, the focus state changes to the near direction while the switch 15 is pushed, as shown by an arrow β1.

When the switch 15 is pushed long when the function of the switch 15 is a focus normal direction function for causing the focus state to change to a normal direction in the image state B or in the state between the image state A and the image state B, the focus state changes to the normal direction while the switch 15 is pushed, as shown by an arrow β2.

If the function of the switch 15 is the focus near direction or the focus normal direction, the focus direction is switched when the switch 15 is pushed shortly, as shown by an arrow β3.

That is, the function of the switch 15 is switched to the focus normal direction by pushing the switch 15 shortly when the function is the focus near direction, and switched to the focus near direction by pushing the switch 15 shortly when the function is the focus normal direction, as shown by arrows β4.

By reciprocating the operation shown by the arrow β4 twice, the focus state is fixed by a process in the CPU as shown by an arrow β5.

When the image state becomes the image state (B) or the image state B, the switch 15 is disabled to function as a zoom switch by the process in the CPU as shown by an arrow β6.

Then, when the switch 15 is pushed long in the image state (B), the function of the switch 15 is switched to the zoom tele direction as shown by an arrow β7, and zooming in the tele direction is started.

If the function of the switch 15 is the zoom tele direction, the zoom state changes to the tele direction while the switch 15 is pushed long, as shown by an arrow β8. However, since the tele end is reached when the image state (BC) is reached, the change of the zoom state to the tele direction does not advance any more.

If the function of the switch 15 is the zoom wide direction in the image state (BC) or in a state between the image state (B) and the image state (BC), the zoom state changes to the wide direction while the switch 15 is pushed long, as shown by an arrow β9.

If the function of the switch 15 is the zoom tele direction or the zoom wide direction, the zoom direction is switched as shown by an arrow β10 when the switch 15 is pushed shortly.

That is, the function of the switch 15 is switched to the zoom wide direction by pushing the switch 15 shortly when the function is the zoom tele direction, and switched to the zoom tele direction by pushing the switch 15 shortly when the function is the zoom wide direction, as shown by arrows β11.

Further, no matter whether the image state is in any of the image state B, the image state (B), the image state (BC), the state between the image state (B) and the image state (BC), the image state returns to the image state A when the operation of the "two successive short pushes" indicated by the arrow outline with a blank inside is performed by the switch 15. When the image state returns to the image state A, the switch 15 is disabled to function as a zoom switch by the process in the CPU, the fixation of the focus state is released so that the switch 15 enters the state of functioning as a focus switch, and the focus switching function is set to the focus near direction, as shown by an arrow β12.

Figure 8:
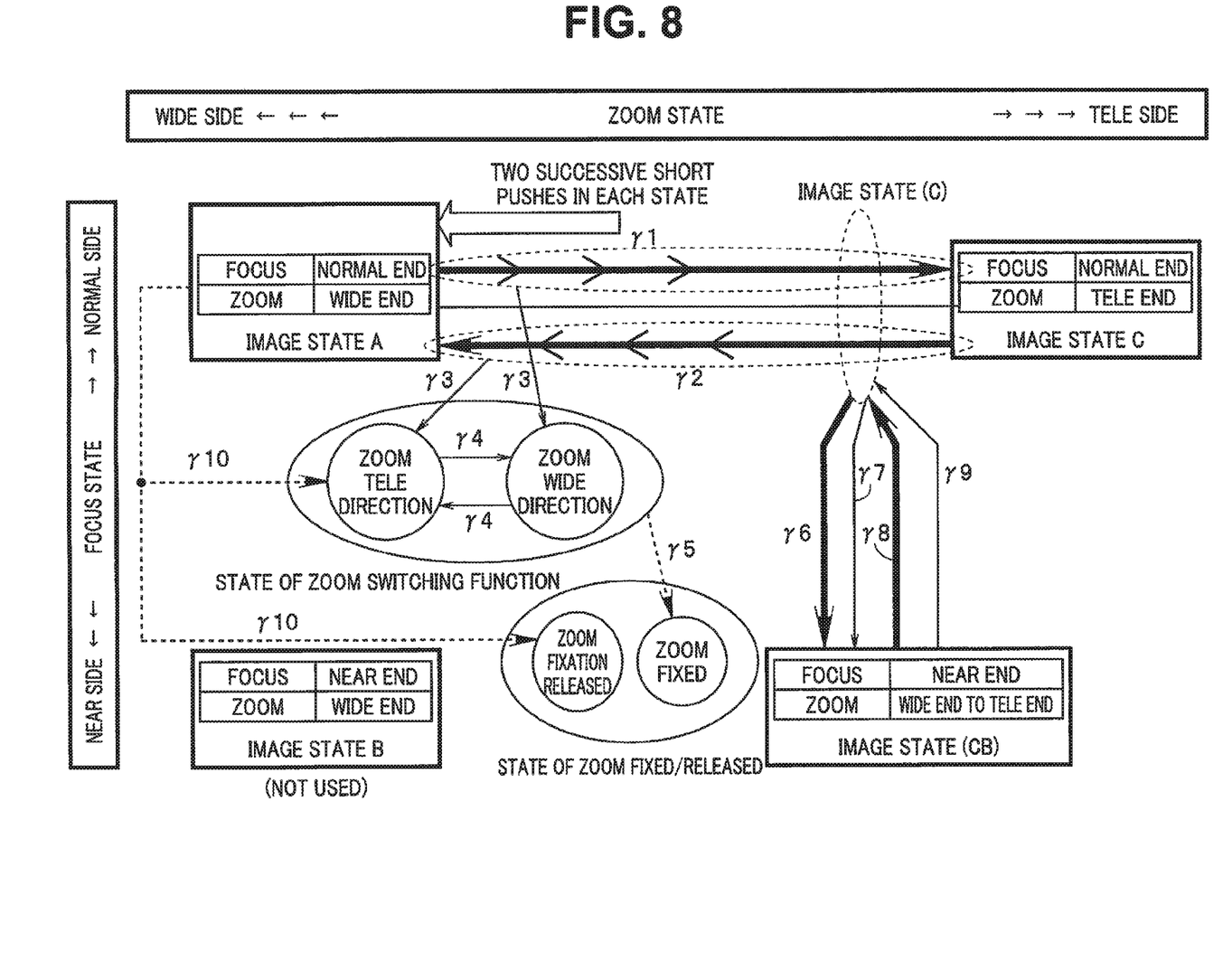
FIG. 8 is a diagram showing an operation of the image pickup system in a zoom priority mode when the two-focus switching is set for focusing, in relation to the first embodiment.

FIG. 8 is a diagram showing an operation of the image pickup system in the zoom priority mode when the two-focus switching is set for focusing.

First, image states A to C are similar to the above description; an image state (C) is a state in which the focus is at the normal end, and the zoom is between the wide end and the tele end (a state between the image state A and the image state C); and an image state (CB) is a state in which the focus is at the near end, and the zoom is between the wide end and the tele end. Note that the image state B is not used in the zoom priority mode when the two-focus switching is set for focusing as shown in FIG. 8.

When the image pickup system is powered on, the image state is switched to the image state A as an initial state.

When the switch 15 is pushed long when the function of the switch 15 is the zoom tele direction in the image state A or in the state between the image state A and the image state C, the zoom state changes to the tele direction while the switch 15 is pushed, as shown by an arrow γ1.

When the switch 15 is pushed long when the function of the switch 15 is the zoom wide direction in the image state C or in the state between the image state A and the image state C, the zoom state changes to the wide direction while the switch 15 is pushed, as shown by an arrow γ2.

If the function of the switch 15 is the zoom tele direction or the zoom wide direction, the focus direction is switched as shown by an arrow γ3 when the switch 15 is pushed shortly.

That is, the function of the switch 15 is switched to the zoom wide direction by pushing the switch 15 shortly when the function is the zoom tele direction, and switched to the zoom tele direction by pushing the switch 15 shortly when the function is the zoom wide direction, as shown by arrows γ4.

By reciprocating the operation shown by the arrow γ4 twice, the zoom state is fixed by the process in the CPU as shown by an arrow γ5.

Further, in the image state (C) in which the focus at a time when the zoom state is fixed is at the normal end, the focus is switched to the near end in both of the case of pushing the switch 15 long as shown by an arrow γ6 and the case of pushing the switch 15 shortly as shown by an arrow V.

On the other hand, in the image state (CB) in which the focus at the time when the zoom state is fixed is at the near end, the focus is switched to the normal end in both of the case of pushing the switch 15 long as shown by an arrow γ8 and the case of pushing the switch 15 shortly as shown by an arrow γ9.

No matter whether the image state is in any of the image state (C), the image state C and the image state (CB), the image state returns to the image state A when the operation of the "two successive short pushes" indicated by the arrow outline with a blank inside is performed by the switch 15. When the image state returns to the image state A, the fixation of the zoom state is released by a process in a CPU, so that the switch 15 enters the state of functioning as a zoom switch, and a zoom switching function is set to the zoom tele direction, as shown by an arrow γ10. Note that, once the zoom state is fixed by a process in the CPU, the fixation of the zoom state is released only by performing the operation of the "two successive short pushes".

Therefore, a usage is adopted in which, in the case of the zoom priority mode, an angle of view is not changed after the angle of view is decided at an initial stage of performing observation by the endoscope 1.

Figure 9:
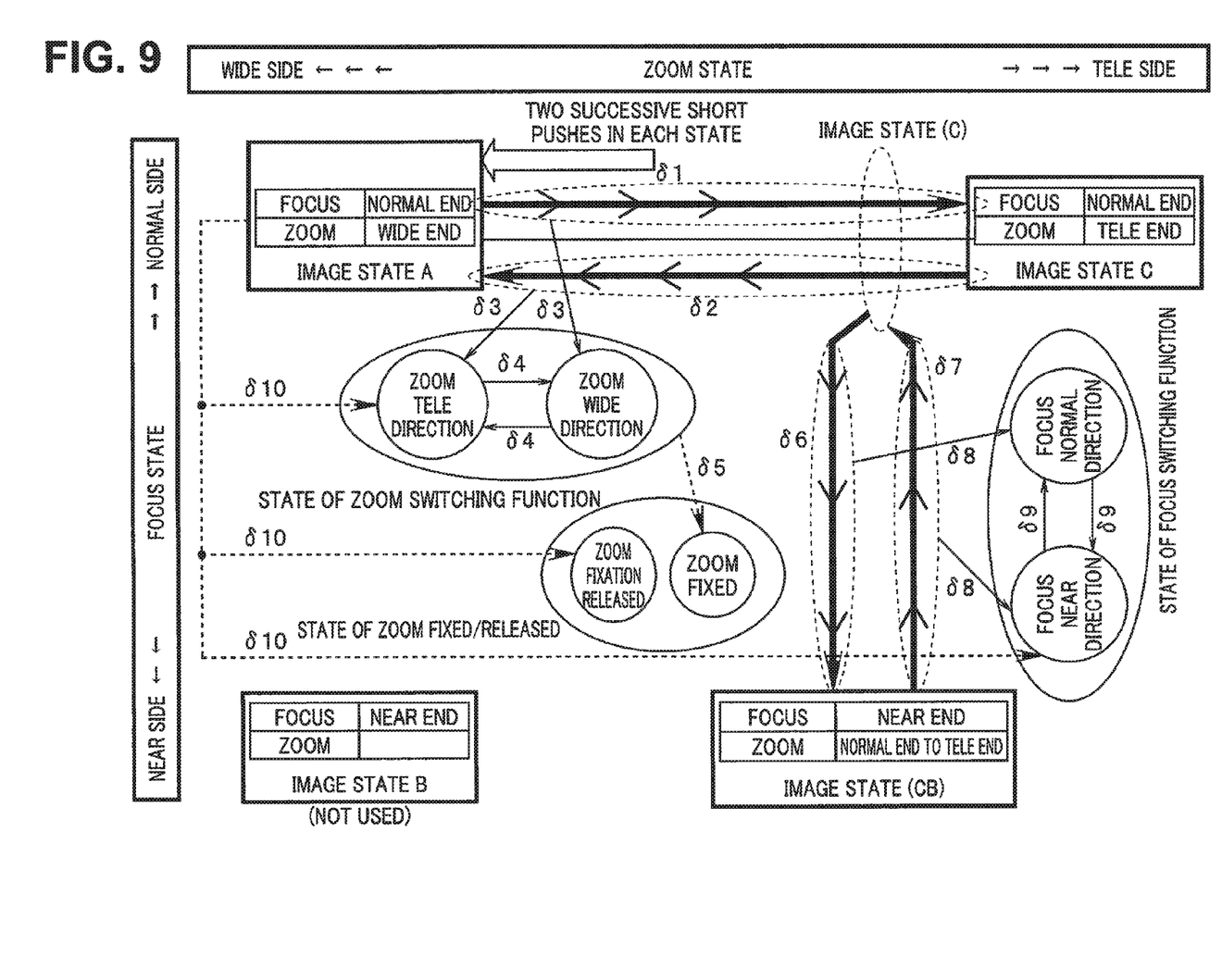
FIG. 9 is a diagram showing an operation of the image pickup system in the zoom priority mode when the seamless focusing operation is set for focusing, in relation to the first embodiment.

FIG. 9 is a diagram showing an operation of the image pickup system in the zoom priority mode when the seamless operation is set for focusing.

First, image states A to C, (C) and (CB) are similar to the above description. Note that the image state B is also not used in the zoom priority mode when the seamless operation is set for focusing as shown in FIG. 9.

When the image pickup system is powered on, the image state is switched to the image state A as an initial state.

When the switch 15 is pushed long when the function of the switch 15 is the zoom tele direction in the image state A or in the state between the image state A and the image state C, the zoom state changes to the tele direction while the switch 15 is pushed, as shown by an arrow δ1.

When the switch 15 is pushed long when the function of the switch 15 is the zoom wide direction in the image state C or in the state between the image state A and the image state C, the zoom state changes to the wide direction while the switch 15 is pushed, as shown by an arrow δ2.

If the function of the switch 15 is the zoom tele direction or the zoom wide direction, the focus direction is switched as shown by an arrow δ3 when the switch 15 is pushed shortly.

That is, the function of the switch 15 is switched to the zoom wide direction by pushing the switch 15 shortly when the function is the zoom tele direction, and switched to the zoom tele direction by pushing the switch 15 shortly when the function is the zoom wide direction, as shown by arrows δ4.

By reciprocating the operation shown by the arrow M twice, the zoom state is fixed by the process in the CPU as shown by an arrow δ5.

Further, if the focus switching function at the time when the zoom state is fixed is the focus near direction, the focus state changes to the near direction when the switch 15 is pushed long, as shown by an arrow δ6.

On the other hand, if the focus switching function at the time when the zoom state is fixed is the focus normal direction, the focus state changes to the normal direction when the switch 15 is pushed long, as shown by an arrow δ7.

If the function of the switch 15 is the focus near direction or the focus normal direction, the focus direction is switched when the switch 15 is pushed shortly, as shown by an arrow δ8.

That is, as shown by an arrow δ9, the function of the switch 15 is switched to the focus normal direction by pushing the switch 15 shortly when the function is the focus near direction, and switched to the focus near direction by pushing the switch 15 shortly when the function is the focus normal direction.

No matter whether the image state is in any of the image state (C), the image state C, a state between the image state (C) and the image state (CB) and the image state (CB), the image state returns to the image state A when the operation of the "two successive short pushes" indicated by the arrow outline with a blank inside is performed by the switch 15. When the image state returns to the image state A, the fixation of the zoom state is released by the process in the CPU, so that the switch 15 enters the state of functioning as a zoom switch, and a zoom switching function is set to the zoom tele direction, as shown by an arrow δ10. Further, the focus switching function is set to the near direction. Note that, once the zoom state is fixed by the process in the CPU, the fixation of the zoom state is released only by performing the operation of the "two successive short pushes".

Therefore, similarly to FIG. 8, the usage is adopted in which, in the case of the zoom priority mode, an angle of view is not changed after the angle of view is decided at an initial stage of performing observation by the endoscope 1.

Note that, in a case where the switch 15 is of a type capable of detecting push force and the like, it is also possible to adopt, for example, strong push/weak push operations of the switch 15 instead of the long push/short push operations of the switch 15 in the above description.

By adopting the configurations shown in FIGS. 4 to 9, it is possible to perform operations which have been conventionally performed by four switches, by one switch, and, therefore, it is possible to resolve the troublesomeness of operating the plurality of switches and improve operability of the endoscope 1.

Further, since the number of switches is reduced, it is possible to contribute to downsizing of the endoscope 1.

Furthermore, since the focus and the zoom are automatically set to the normal end and the wide end, respectively, when power is turned on, it is possible to perform panoramic observation without a separate operation being required.

By performing only a simple operation of two successive short pushes on the switch 15, it is possible to perform quickly panoramic observation similar to that performed when power is turned on.

In addition, since the priority mode display 52 is displayed on the monitor 5, it is possible to grasp the state of the switch 15. Furthermore, since the focus position display 53 is displayed on the monitor 5, it is possible to continuously grasp the focus state. In addition, since the zoom position display 54 is displayed on the monitor 5, it is possible to continuously grasp the zoom state. Thus, it is possible for a surgeon to easily grasp the state of the endoscope 1 during observation.

Note that, though an image pickup system has been mainly described above, a method for operating the image pickup system, a processing program for causing a computer to execute the method for operating the image pickup system, a computer-readable non-temporary recording medium in which the processing program is recorded, and the like are also possible.

Note that the present invention is not limited to the above-described embodiments as they are, and it is possible to vary the components at a stage of practicing the present invention in order to embody them within a range not departing from the gist of the present invention. Further, various aspects of the invention can be formed by appropriate combinations of a plurality of components disclosed in the above embodiments. For example, some components may be removed from all the components shown in the embodiments. Furthermore, components among the different embodiments may be appropriately combined. Thus, various variations and applications are, of course, possible within the range not departing from the spirit of the invention.

What is claimed is:

1. An image pickup system for endoscope comprising:
a light source radiating illuminating light to a subject;
an image forming optical system forming an optical image of reflected light reflected from the subject out of the illuminating light radiated by the light source;
a driving section driving a focus lens, the focus lens being a part of the image forming optical system, within a predetermined movable range;
an image pickup section picking up the optical image formed by the image forming optical system and outputting an image signal;
an amplifying section signal-amplifying the image signal outputted from the image pickup section according to an amplification factor;
a brightness detecting section detecting brightness of the image indicated by the image signal;
a brightness adjusting section adjusting a brightness control condition for, if the brightness of the image detected by the brightness detecting section changes, controlling at least one parameter among a condition of a light quantity by the light source, a condition of image pickup by the image pickup section and the amplification factor of the amplifying section so that the brightness of the image becomes a predetermined brightness;
an auxiliary autofocus section estimating a subject distance corresponding to when the brightness of the image becomes the predetermined brightness as a temporary focus position of the optical image with respect to a subject distance indicated by a multivariable function of the brightness control condition adjusted by the brightness adjusting section;
and determining a range which includes the temporary focus position and is smaller than the predetermined movable range as a scanning range; and
a contrast autofocus section causing the driving section to drive the focus lens to perform contrast autofocus based on the scanning range determined by the auxiliary autofocus section.

2. The image pickup system for endoscope according to claim 1, wherein
the light source has a light quantity diaphragm for controlling the light quantity of the illuminating light; and
the light quantity condition is a diaphragm value of the light quantity diaphragm.

3. The image pickup system for endoscope according to claim 1, wherein
the light source is configured so as to control the light quantity of the illuminating light by pulse-width control; and
the light quantity condition is a pulse width in the pulse-width control.

4. The image pickup system for endoscope according to claim 1, wherein
the image pickup section is configured such that an exposure time period is variable as the image pickup condition.

5. A method for operating an image pickup system for endoscope comprising the steps of:
radiating illuminating light to a subject, by a light source;
driving a focus lens, the focus lens being a part of an image forming optical system forming an optical image of reflected light reflected from the subject out of the illuminating light radiated by the light source, within a predetermined movable range, by a driving section;
picking up the optical image formed by the image forming optical system and outputting an image signal, by an image pickup section;
signal-amplifying the image signal outputted from the image pickup section according to an amplification factor, by an amplifying section;
detecting brightness of the image indicated by the image signal, by a brightness detecting section;
adjusting a brightness control condition for, if the brightness of the image detected by the brightness detecting section changes, controlling at least one parameter among a condition of a light quantity by the light source, a condition of image pickup by the image pickup section and the amplification factor of the amplifying section so that the brightness of the image becomes a predetermined brightness, by a brightness adjusting section;

estimating a subject distance corresponding to when the brightness of the image becomes the predetermined brightness as a temporary focus position of the optical image with respect to a subject distance indicated by a multivariable function of the brightness control condition adjusted by the brightness adjusting section, and determining a range which includes the temporary focus position and is smaller than the predetermined movable range as a scanning range, by an auxiliary autofocus section; and causing the driving section to drive the focus lens to perform contrast autofocus based on the scanning range determined by the auxiliary autofocus section, by a contrast autofocus section.

\* \* \* \* \*

UNITED STATES PATENT AND TRADEMARK OFFICE
CERTIFICATE OF CORRECTION

PATENT NO. : 9,621,814 B2  Page 1 of 1
APPLICATION NO. : 15/069320
DATED : April 11, 2017
INVENTOR(S) : Takehide Fujimoto et al.

It is certified that error appears in the above-identified patent and that said Letters Patent is hereby corrected as shown below:

On the Title Page

Item (54) and in the Specification, Column 1, Lines 1-3, should read:
IMAGE PICKUP SYSTEM FOR ENDOSCOPE AND METHOD FOR OPERATING IMAGE PICKUP SYSTEM FOR ENDOSCOPE

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*